United States Patent [19]

Magnus

[11] Patent Number: 5,471,983
[45] Date of Patent: Dec. 5, 1995

[54] ELECTRODE BRACELET FOR DETECTING THE PHYSIOLOGICAL ELECTRIC POTENTIAL OF A PATIENT'S LIMB

[75] Inventor: Hans F. Magnus, Castelgabbiano, Italy

[73] Assignee: Vega Marketing Ltd., London, England

[21] Appl. No.: 93,061

[22] Filed: Jul. 16, 1993

[30] Foreign Application Priority Data

Jul. 17, 1992 [IT] Italy .................. TO92U0188
Jul. 17, 1992 [IT] Italy .................. TO92U0190

[51] Int. Cl.[6] ........................... A61B 5/0408
[52] U.S. Cl. ................. 128/644; 128/639; 607/149
[58] Field of Search .................. 128/644, 639, 128/640; 607/149, 139

[56] References Cited

U.S. PATENT DOCUMENTS

| | | | |
|---|---|---|---|
| 2,621,657 | 12/1952 | Leech | 128/417 |
| 2,815,749 | 12/1957 | Friedman | 128/644 |
| 3,323,516 | 6/1967 | Salter | 128/644 |
| 3,572,323 | 3/1971 | Yuan | 128/640 |
| 3,971,366 | 7/1976 | Montoyama | 128/2.1 Z |
| 4,448,199 | 5/1984 | Schmid | 128/644 |
| 4,809,700 | 3/1989 | Castelli | 128/644 |

FOREIGN PATENT DOCUMENTS

| | | | |
|---|---|---|---|
| 0159434 | 10/1985 | European Pat. Off. | 128/644 |
| 1227691 | 3/1960 | France | 128/644 |
| 2643811 | 3/1989 | France . | |
| 3709055 | 9/1987 | Germany . | |
| 9112497 | 12/1991 | Germany . | |
| 639496 | 3/1962 | Italy | 128/644 |
| 992022 | 1/1983 | U.S.S.R. | 128/644 |

*Primary Examiner*—Lee S. Cohen
*Attorney, Agent, or Firm*—Ladas & Parry

[57] ABSTRACT

A bracelet comprising at least one band of physiologically compatible material deformable elastically in a direction perpendicular to the band, which is preloaded in the form of a C, and presents a first arm fitted with an electrode having a pad, and a second arm with nonslip means, e.g. in the form of ribs or teeth. The bracelet is fitted on to the limb by parting the arms of the band, the residual elastic deformation of which exerts such pressure on the electrode as to hold it in place contacting the skin. At the same time, the nonslip means produce a temporary impression in the skin, for preventing both axial and angular slippage of the bracelet in relation to the limb.

12 Claims, 3 Drawing Sheets

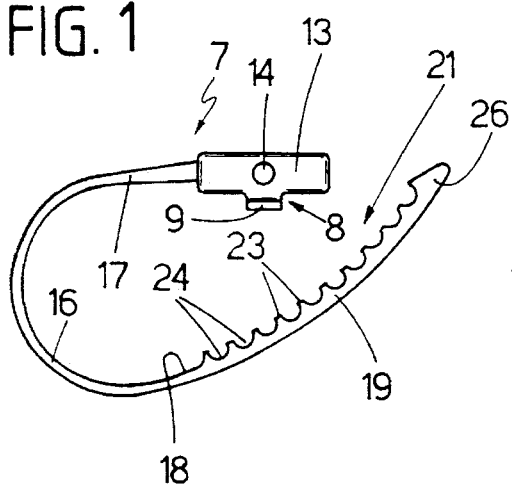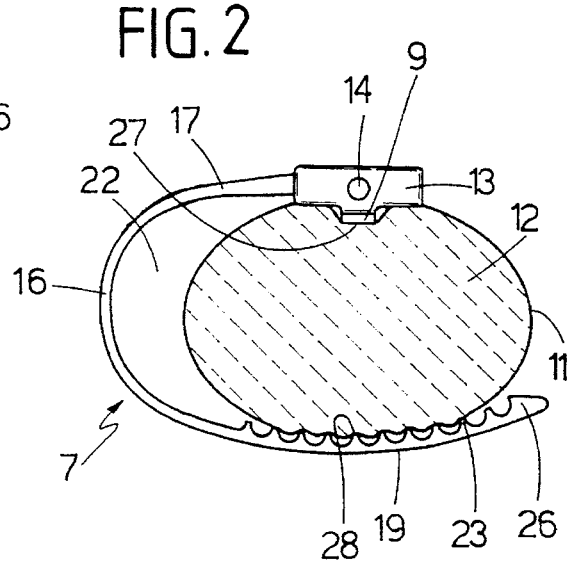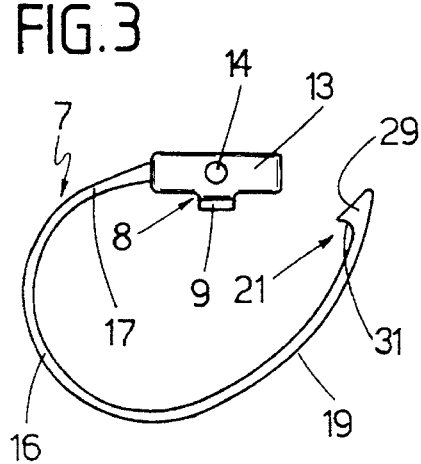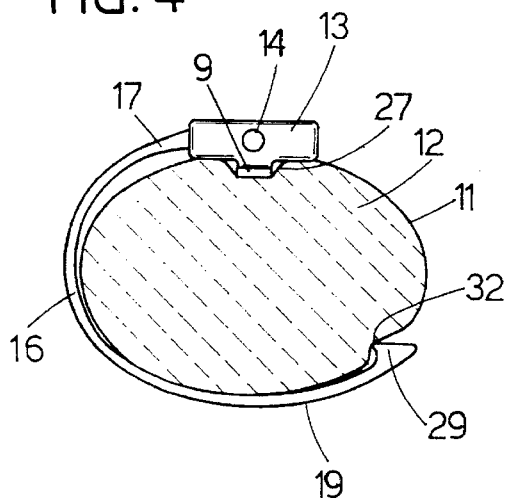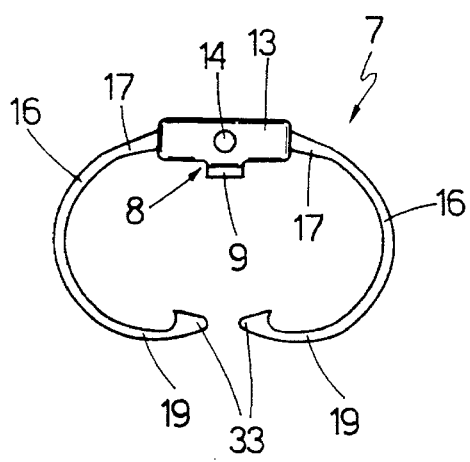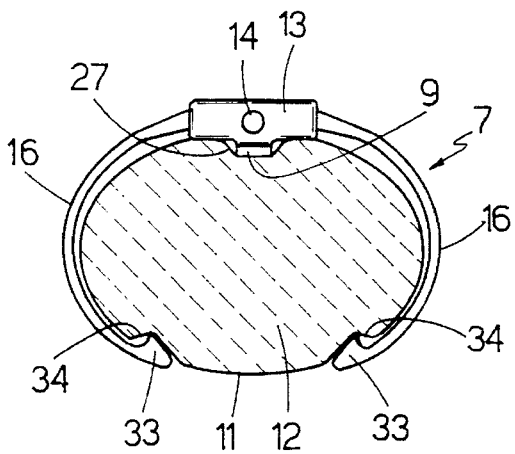

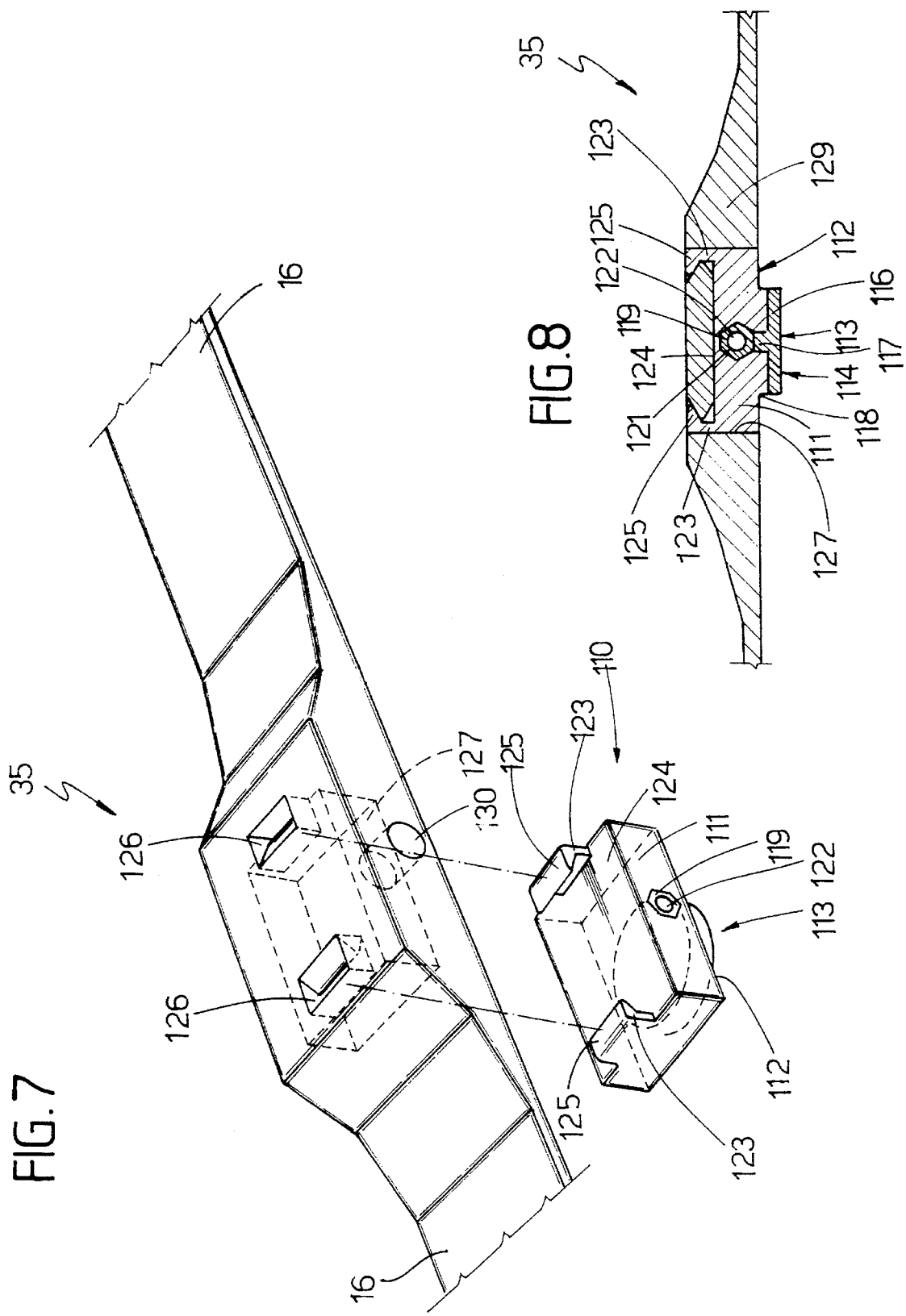

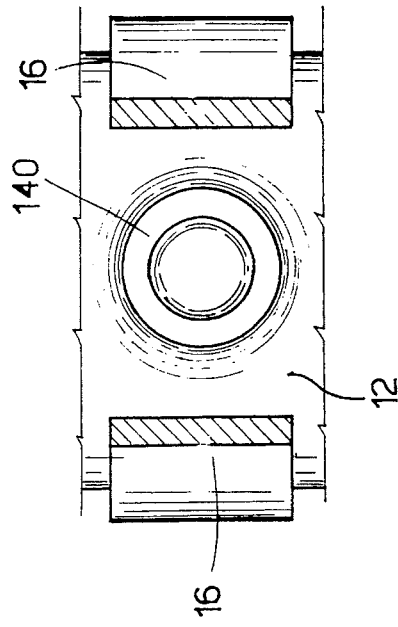
FIG.11
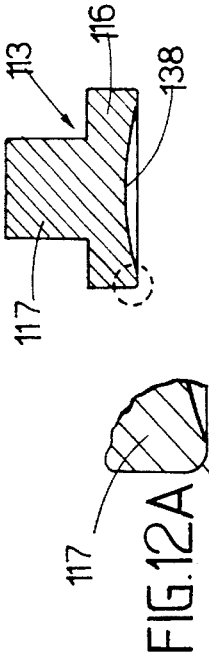
FIG.12
FIG.12A
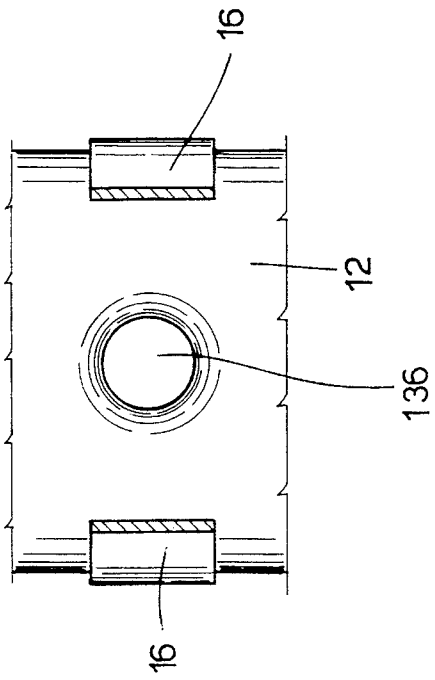
FIG.13
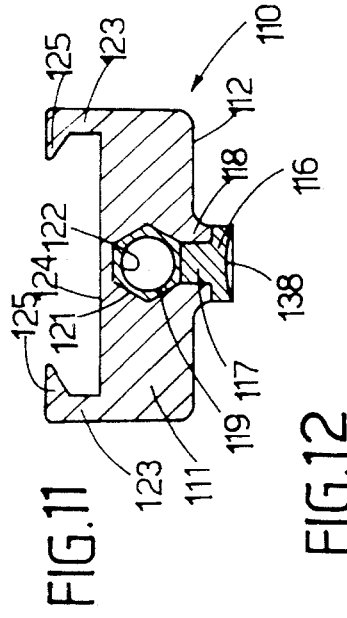
FIG.9
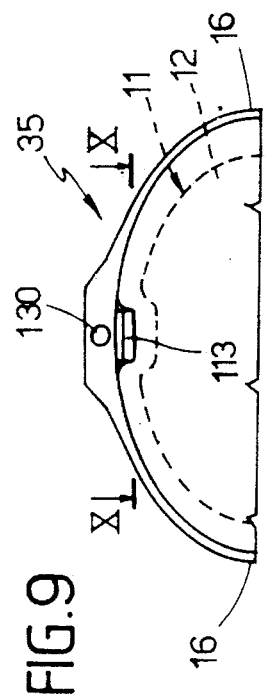
FIG.10

5,471,983

ELECTRODE BRACELET FOR DETECTING THE PHYSIOLOGICAL ELECTRIC POTENTIAL OF A PATIENT'S LIMB

BACKGROUND OF THE INVENTION

The present invention relates to an electrode bracelet, for electrocardiographic equipment, for detecting the physiological electric potential of a patient's limb.

As we know, on electrocardiographic equipment, the physiological electric potential of the patient is detected by affixing electrodes to given portions of the patient's skin. For limb applications in particular, the electrode is fitted to a supporting bracelet so as to present a pad of electrically conductive material facing the skin, and a layer of conductive paste is applied between the skin and pad.

The pad itself is normally set inside a support on the bracelet, either set back or flush with the contact surface of the support, so that electric connection between the skin and pad depends exclusively on the conductivity of the paste.

The band of the bracelet, on the other hand, is normally made of flexible, physiologically compatible material, is fitted about the limb so as press the electrode against the skin, and is normally fastened by means of a buckle or press stud.

In the course of the recording, however, due to movement of the patient, physical changes in skin condition, and the varying diameter of the limb, known bracelets of the aforementioned type invariably slide over the skin, thus resulting in both discomfort to the patient and disturbance of the electric output signal. What is more, in view of the very small electric potential being recorded, such disturbance so entirely offsets the output signal that the electrocardiogram frequently has to be repeated.

A further drawback of known bracelets of the aforementioned type is the relatively complex, time-consuming operation required for fitment to the limb.

SUMMARY OF THE INVENTION

It is an object of the present invention to provide a highly straightforward electrode bracelet of the aforementioned type, designed to overcome the aforementioned drawbacks.

According to the present invention, there is provided an electrode bracelet for detecting the physiological electric potential of a patient's limb, the bracelet comprising at least one band of physiologically compatible material, and an electrode fitted to said band; characterized by the fact that said physiologically compatible material is deformable elastically in a direction perpendicular to the surface of said band, which is so shaped and sized as to grip said limb and exert on said electrode a predetermined elastic pressure in relation to the skin of said limb.

The electrode of the bracelet as described above preferably comprises a pad of electrically conductive material fitted to a support of insulating material having a surface designed to contact the patient's skin; the pad being fitted to the support so as to project from said surface, so that, in use, the pressure exerted by the pad is such as to produce a temporary impression on the patient's skin.

BRIEF DESCRIPTION OF THE DRAWINGS

A preferred, non-limiting embodiment of the present invention will be described by way of example with reference to the accompanying drawings, in which:

FIGS. 1 and 2 show respective idle and as-fitted views of an electrode bracelet in accordance with a first variation of the present invention;

FIGS. 3 and 4 show similar views of a bracelet in accordance with a further variation of the present invention;

FIGS. 5 and 6 show similar views of a bracelet in accordance with a third variation of the present invention;

FIG. 7 shows a partial exploded view in perspective of a further preferred embodiment of the bracelet according to the present invention;

FIG. 8 shows a partial longitudinal section of the FIG. 7 bracelet;

FIG. 9 shows a partial schematic view of the FIG. 7 bracelet fitted to the patient's limb;

FIG. 10 shows a section along line X—X in FIG. 9;

FIG. 11 shows a section of a variation of a detail in FIG. 7;

FIG. 12 shows a larger-scale section of a detail in FIG. 11;

FIG. 12A shows a larger-scale section of a detail in FIG. 12;

FIG. 13 shows the same section as in FIG. 10 with the FIG. 11 detail.

DETAILED DESCRIPTION OF THE INVENTION

Number 7 in the accompanying drawings indicates a bracelet for an electrode 8 comprising a pad 9 of electrically conductive material designed to contact the skin 11 of a patient's limb 12, e.g. the arm, for detecting its physiological electric potential. Bracelet 7 comprises a block 13 housing electrode 8; and a seat 14 in which to insert the connecting pin of the electrocardiographic equipment.

Bracelet 7 also comprises at least one band 16 of physiologically compatible material connected to or forming one piece with block 13. According to the present invention, band 16 is made of material deformable elastically in a direction perpendicular to the surface of band 16, e.g. plastic material of the type known as Delrin (registered trade mark).

Band 16 is C-shaped, is so designed in terms of length, width and thickness as to present a predetermined elastic force, and is elastically preloaded so as to assume, when idle, the configurations shown in FIGS. 1, 3 and 5. One arm 17 of C-shaped band 16 presents block 13 on the end, while the inner face 18 of the other arm 19 presents nonslip means indicated as a whole by 21.

According to the FIGS. 1–2 variation, bracelet 7 presents a single elongated C-shaped band 16 designed to grip limb 12 between arms 17 and 19, leaving an ample vacant loop 22; and nonslip means 21 comprise a series of ribs 23 crosswise in relation to the axis of band 16.

Ribs 23 are separated by curved-section grooves 24, and cover substantially the whole of arm 19. The end rib on arm 19 consists of an asymmetrical-toothed appendix 26 having a hook-shaped face consisting of part of adjacent groove 24.

The bracelet is fitted on to limb 12 by first coating the relative portion of skin 11 with the usual conductive paste, and then elastically deforming band 16 so as to part arms 17 and 19 and fit the band on to limb 12. When band 16 is released on to limb 12, it springs back partially so as to exert elastic force on pad 9 and so produce temporary impression 27 on the skin.

At the same time, arm 19 of band 16 presses on the opposite side of limb 12, and ribs 23 and tooth 26 create respective temporary impressions 28 in skin 11 preventing both axial and angular slippage of bracelet 7 in relation to limb 12. In the case of relatively thin limbs 12, as shown in FIG. 2, one or more ribs 23 and/or tooth 26 may fail to engage skin 11. For the sake of clarity, the depth of impressions 27 and 28 is exaggerated in FIG. 2.

According to the FIGS. 3–4 variation, bracelet 7 again presents a single C-shaped band 16, which in this case, however, wraps around at least half the circumference of limb 12; and nonslip means 21 consist of a single asymmetrical tooth 29 located on the end of arm 19 and having a hook-shaped face 31 facing the opposite way to the end of arm 19.

The FIG. 3 bracelet is fitted to limb 12 in the same way as that of FIG. 1 and therefore requires no further description. In this case, tooth 29 produces only one impression 32 in skin 11, but the accentuated curve of the end of arm 19 and the asymmetrical section of tooth 29 provide for effectively preventing angular slippage of the bracelet in relation to limb 12.

According to the FIGS. 5–6 variation, bracelet 7 is a dual-wrap-around type featuring two symmetrical, wrap-around, C-shaped bands 16, each designed to wrap around less than half the circumference of limb 12; and nonslip means 21 on arm 19 of each band 16 consist of a tooth 33 similar to 29 in FIGS. 3 and 4.

The FIG.5 bracelet is fitted on to limb 12 in the same way as that of FIG. 3, by acting simultaneously on arm 19 of both bands 16. In this case, teeth 33 produce two temporary impressions 34 in the skin, which are equally effective in preventing angular slippage of bracelet 7 in either direction of rotation.

The FIG. 7 embodiment relates to a bracelet 35 similar to bracelet 7 in FIG. 5 and comprising an electrode 110 for detecting the electric potential of limb 12. Electrode 110 comprises a substantially parallelepiped support 111 of preferably plastic insulating material, and having a bottom surface 112 (FIG. 8) designed, in use, to contact a given portion of skin 11 of limb 12.

Electrode 110 comprises a pad 113 of electrically conductive material, e.g. surface chloridized silver, fitted to support 111 and which, in use, is designed to contact skin 11, possibly via the interposition of a film of normal conductive paste. According to the present invention, pad 113 is fitted to support 111 so as to present an active contact surface 114 projecting slightly from surface 112 of support 111.

Pad 113 consists of a circular plate 116 forming one piece with a stem 117 and resting on a shallow projection 118 of support 111. Stem 117 contacts a bush 119 arranged transversely inside support 111, with its axis parallel to surface 112, and having a prismatic outer surface 121 and a hole 122 in which to insert the connecting pin of the electrocardiographic equipment.

Plate 116 and bush 119 may be in the form of inserts inside support 111, as per safety standards governing electrochemical electrode-skin contact characteristics. Support 111 is also formed in one piece with two hook-shaped appendixes 123 extending from surface 124 opposite surface 112.

Appendixes 123 are both in the form of an upside down L comprising a substantially wedge-shaped tab 125, and click inside respective openings 126 (FIG. 7) in a seat 127 formed in bracelet 35 and designed to receive electrode 110. Tabs 125 click inside a flared portion at the top end of openings 126.

In actual use, bands 16 press electrode 110 on to limb 12, so that surface 112 adheres to skin 11 of limb 12 with a small amount of overall pressure, and so that active surface 114 of plate 116 produces a temporary impression 136 in skin 11, for ensuring perfect transmission of the potential from skin 11 to pad 113, and preventing any accidental slippage of pad 113 over skin 11.

For a given overall pressure of electrode 110 on skin 11, pad 113 provides for greater specific pressure on skin 11 as compared with traditional electrodes. As such, the surface of plate 116 may be reduced drastically as compared with that of traditional pads, thus enabling a reduction in the portion of skin 11 to be coated with conductive paste, and obvious advantages in terms of both comfort of the patient and the production cost of electrode 110. By way of example, surface 114 may be reduced to less than 60 sq.mm, and, in the case of a circular surface, its diameter may advantageously range between 4 and 8 mm.

According to a further variation shown in FIGS. 11 to 13, plate 116 of pad 113 presents a slightly concave active contact surface 138, and a rounded peripheral edge 139 for reducing discomfort to the patient. In this case, surface 138 produces an annular temporary impression 140 in skin 11, and, for a given diameter of plate 116, provides for greater specific pressure on skin 11 as compared with the FIGS. 8–10 embodiment.

The advantages of electrode bracelets 7 and 35 according to the present invention will be clear from the foregoing description. In particular, they provide for dispensing with buckles or press studs; and for preventing both axial and angular slippage of the bracelet over the skin. Bracelet 35 in particular provides for considerable specific pressure of pad 113 on skin 11, and for drastically reducing transverse slippage of electrode 110 over skin 11, thus eliminating any disturbance of the ECG recording, especially in the event of movement or excitability on the part of the patient.

To those skilled in the art it will be clear that changes may be made to bracelets 7 and 35 as described and illustrated herein without, however, departing from the scope of the present invention. For example, in the case of bracelet 7, electrode 8 may be fitted in removable manner to block 13, and bands 16 may consist of a plastic outer layer over a flexible metal blade. In the case of bracelet 35, plate 116 may be oblong as opposed to circular, and electrode 110 may be fitted to bracelets other than that described, for fitment to various parts of the patient's body. Finally, in the case of both bracelets 7 and 35, respective pads 9 and 113 need not necessarily project in relation to the supporting surface of the bracelet on limb 12.

I claim:

1. An electrode bracelet for detecting the physiological electric potential of a patient's limb comprising at least one C-shaped band having an inner surface adapted to wrap at least partially around said limb, said band being made of a physiologically compatible material and is deformable elastically in a direction perpendicular to said inner surface, a first end of said band being provided with a hook-shaped appendix crosswise in relation to a longitudinal axis of said inner surface, and an electrode fitted into a section of said band for contacting a portion of skin of said limb, said electrode comprising a pad of conductive material fitted to a support of insulating material, said support having a contact surface flush with said inner surface, said pad being formed as an insert with said support as to project from said contact surface, said band being so sized as to exert a predetermined elastic pressure to cause said appendix and said pad to produce temporary impressions in said skin for preventing a slippage of both said band and said pad in relation to said limb.

2. A bracelet as claimed in claim 1, wherein said elastically deformable material is a plastic material known as Delrin (registered trade mark).

3. A bracelet as claimed in claim 1, wherein said inner surface comprises a series of ribs crosswise in relation to the longitudinal axis of said band.

4. A bracelet as claimed in claim 1 comprising two C-shaped bands wherein said bands are symmetrical to each other; each said band having an inner surface, and each band being deformable elastically in a direction perpendicular to said inner surface; each said band being shaped to wrap around less than half the circumference of said limb; each said band having a first end and a second end, each said first end being fitted with said electrode; and each said second end terminating in an asymmetrical-toothed appendix crosswise in relation to the longitudinal axis of each said band.

5. A bracelet as claimed in claim 1, wherein said support is provided with a shallow projection projecting from said contacting surface, said pad including a plate integral with a shank inserted into said support, so that said plate rests on said shallow projection.

6. A bracelet as claimed in claim 5 wherein said pad presents an active contact surface with an area of less than 60 sq. mm. for forming said impression wherein said active contact surface has an outer edge.

7. A bracelet as claimed in claim 6, wherein said active contact surface is flat and circular in shape with a diameter of between 4 and 8 mm.

8. A bracelet as claimed in claim 6 wherein said active contact surface of said pad is concave, so that said impression is annular in shape.

9. A bracelet as claimed in claim 6, wherein the outer edge of said active surface is rounded.

10. A bracelet as claimed in claim 5 wherein said support further comprises a conductive bush contacting said shank wherein said bush extends transversely, parallel to an active contact surface of said pad and is engageable by a pin.

11. A bracelet as claimed in claim 1, wherein said section of said band is provided on a second end of said band.

12. A bracelet as claimed in claim 1, wherein said section of said band is formed of a central section of said band and wherein said band includes a second end symmetric with said first end and provided with another hook-shaped appendix crosswise in relation to said longitudinal axis.

* * * * *